（12）United States Patent
　　　Sitnikov et al.

(10) Patent No.: US 10,558,198 B2
(45) Date of Patent: Feb. 11, 2020

(54) ONSITE MOBILE MANUFACTURING PLATFORM

(71) Applicant: Mueller International, LLC, Atlanta, GA (US)

(72) Inventors: Timofey Sitnikov, Harrison, TN (US); Jason White Bradley, Soddy Daisy, TN (US); Paul Gifford, Chattanooga, TN (US); Aurelian Ioan Furcoiu, Chattanooga, TN (US)

(73) Assignee: Mueller International, LLC, Atlanta, GA (US)

( * ) Notice: Subject to any disclaimer, the term of this patent is extended or adjusted under 35 U.S.C. 154(b) by 158 days.

(21) Appl. No.: 15/694,304

(22) Filed: Sep. 1, 2017

(65) Prior Publication Data

US 2019/0072932 A1　　Mar. 7, 2019

(51) Int. Cl.
| | |
|---|---|
| *G05B 19/4099* | (2006.01) |
| *H04N 1/00* | (2006.01) |
| *G06T 17/00* | (2006.01) |
| *G01N 3/08* | (2006.01) |
| *B29C 64/20* | (2017.01) |
| *B29C 64/393* | (2017.01) |
| *B33Y 10/00* | (2015.01) |
| *B33Y 30/00* | (2015.01) |
| *B33Y 50/02* | (2015.01) |

(52) U.S. Cl.
CPC .......... *G05B 19/4099* (2013.01); *B29C 64/20* (2017.08); *B29C 64/393* (2017.08); *B33Y 10/00* (2014.12); *B33Y 30/00* (2014.12); *B33Y 50/02* (2014.12); *G06T 17/00* (2013.01); *H04N 1/00827* (2013.01); *G01N 3/08* (2013.01); *G01N 2203/0017* (2013.01); *G05B 2219/35134* (2013.01); *G05B 2219/49023* (2013.01)

(58) Field of Classification Search
CPC ...... G05B 19/4099; G05B 2219/49023; G05B 2219/35134; B33Y 10/00; B33Y 50/02; B33Y 30/00; G06T 17/00; H04N 1/00827; B29C 64/393; B29C 64/20; G01N 2203/0017; G01N 3/08
See application file for complete search history.

(56) References Cited

U.S. PATENT DOCUMENTS

| 9,562,632 | B1 * | 2/2017 | Billman | ................ G01S 7/4817 |
| 2002/0035773 | A1 * | 3/2002 | Dubuc | ..................... B60P 3/14 |
| | | | | 29/428 |
| 2004/0148753 | A1 * | 8/2004 | Dubuc | ..................... B60P 3/14 |
| | | | | 29/428 |

(Continued)

*Primary Examiner* — Charles R Kasenge
(74) *Attorney, Agent, or Firm* — Taylor English Duma LLP

(57) ABSTRACT

A method of manufacturing a component of a water infrastructure system can include carrying a mobile manufacturing platform with a vehicle from a storage site to a worksite located remotely from the storage site, the mobile manufacturing platform including a control unit; and a manufacturing unit operatively coupled to the control unit; sending the solid model of a first component or an equivalent thereof to the manufacturing unit; fabricating a second component using an automated manufacturing process based on the solid model of the first component saved on a computer-readable storage medium operatively coupled to the control unit; and returning the system from the worksite to the storage site.

18 Claims, 9 Drawing Sheets

(56) References Cited

U.S. PATENT DOCUMENTS

| | | | |
|---|---|---|---|
| 2013/0196104 A1* | 8/2013 | Matsumoto | C08L 79/08 428/36.92 |
| 2014/0300753 A1* | 10/2014 | Yin | G01J 3/50 348/187 |
| 2018/0001389 A1* | 1/2018 | Atin | G01B 11/24 |

* cited by examiner

ONSITE MOBILE MANUFACTURING PLATFORM

TECHNICAL FIELD

Field of Use

This disclosure relates to mobile manufacturing systems. More specifically, this disclosure relates to a system able to specify, fabricate, and evaluate a component of a water infrastructure system or other systems onsite.

Related Art

Repair of any large system including a water infrastructure system can require the replacement of certain components. Sometimes such a repair can be predicted, but sometimes it can be required without warning at an inopportune time or in a remote location of the system. When a unique component that a serviceperson does not have "on hand" requires replacement, the time it takes to order, build, ship, and receive the replacement component can take days or weeks. Sometimes the replacement part is needed sooner than possible with conventional methods.

SUMMARY

It is to be understood that this summary is not an extensive overview of the disclosure. This summary is exemplary and not restrictive, and it is intended to neither identify key or critical elements of the disclosure nor delineate the scope thereof. The sole purpose of this summary is to explain and exemplify certain concepts of the disclosure as an introduction to the following complete and extensive detailed description.

In one aspect, disclosed is a mobile manufacturing system comprising: a control unit configured for ready portable transport via a vehicle from a storage site to a worksite and then back to the storage site, the worksite located remotely from the storage site; a three-dimensional scanner operatively coupled to the control unit and configured for portable transport via the vehicle to the worksite, the scanner configured to convert the geometry of a first component of a water infrastructure system into electronic data based on a physical scan of the first component, a one of the scanner and the control unit comprising a converter configured to convert the data into a three-dimensional solid model of the first component; and a manufacturing unit operatively coupled to the control unit and configured for ready portable transport via a vehicle to the worksite, the manufacturing unit configured to fabricate a second component of the water infrastructure system using an automated manufacturing process based on the solid model of the first component.

In a further aspect, disclosed is a mobile manufacturing system comprising: a server comprising a computer-readable storage medium, the computer-readable storage medium configured to selectively store data sufficient for defining at least a portion of specifications of a first component, the server further configured to selectively send the data to and receive the data from a certification agency; a mobile manufacturing platform configured for transport via a vehicle to a worksite, the platform comprising: a control unit operatively coupled to the server; a three-dimensional scanner operatively coupled to the control unit, the scanner configured to convert geometry of the first component into electronic data based on a physical scan of the first component; a one of the control unit and the scanner comprising a converter configured to convert the data into a three-dimensional solid model of the first component; a manufacturing unit operatively coupled to the control unit, the manufacturing unit configured to fabricate a second component using an automated manufacturing process based on the solid model of the first component stored on the server; a quality test unit operatively coupled to the control unit and configured to perform testing on the second component and on dog bone samples of a batch of a material used to fabricate the second component; a material recycle unit operatively coupled to the control unit and configured to receive the first component for disposal; and a power unit configured to power at least one of the control unit, the scanner, the manufacturing unit, the quality test unit, and the material recycle unit; the power unit comprising a power source comprising at least one of a battery and a generator.

In yet another aspect, disclosed is a method of manufacturing a component of a water infrastructure system, the method comprising: carrying a mobile manufacturing platform with a vehicle from a storage site to a worksite located remotely from the storage site, the mobile manufacturing platform comprising: a control unit; and a manufacturing unit operatively coupled to the control unit; sending the solid model of a first component or an equivalent thereof to the manufacturing unit; fabricating a second component using an automated manufacturing process based on the solid model of the first component saved on a computer-readable storage medium operatively coupled to the control unit; and returning the system from the worksite to the storage site.

Various implementations described in the present disclosure may comprise additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims. The features and advantages of such implementations may be realized and obtained by means of the systems, methods, features particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

The accompanying drawings, which are incorporated in and constitute a part of this specification, illustrate several aspects of the disclosure and together with the description, serve to explain various principles of the disclosure. The drawings are not necessarily drawn to scale. Corresponding features and components throughout the figures may be designated by matching reference characters for the sake of consistency and clarity.

DETAILED DESCRIPTION

Figure 1:
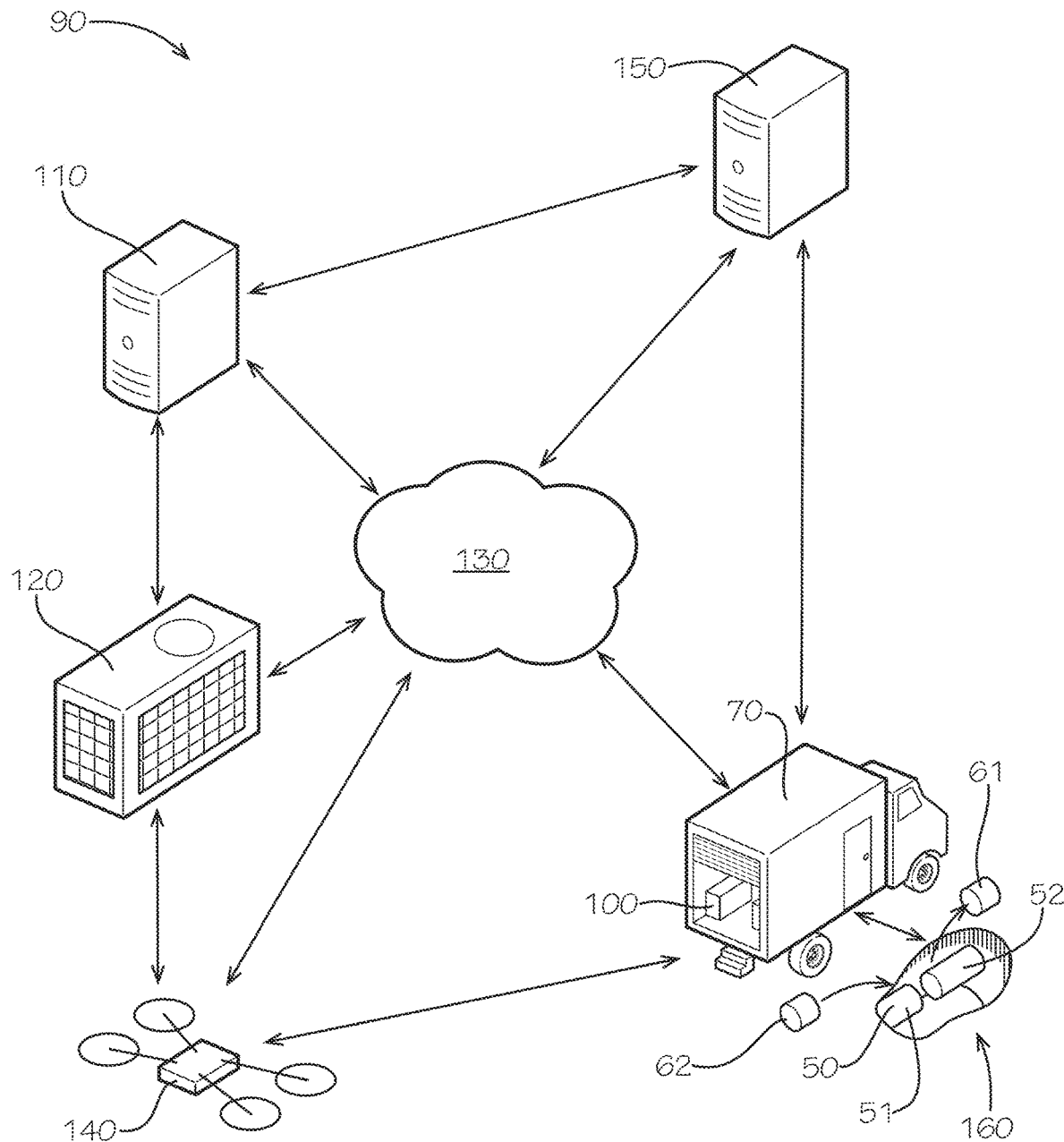
FIG. 1 is a network diagram of a mobile manufacturing system comprising a mobile manufacturing platform, in accordance with one aspect of the current disclosure.

The present disclosure can be understood more readily by reference to the following detailed description, examples, drawings, and claims, and their previous and following description. However, before the present devices, systems, and/or methods are disclosed and described, it is to be understood that this disclosure is not limited to the specific devices, systems, and/or methods disclosed unless otherwise specified, as such can, of course, vary. It is also to be understood that the terminology used herein is for the purpose of describing particular aspects only and is not intended to be limiting.

The following description is provided as an enabling teaching of the present devices, systems, and/or methods in their best, currently known aspect. To this end, those skilled in the relevant art will recognize and appreciate that many changes can be made to the various aspects described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

As used throughout, the singular forms "a," "an" and "the" include plural referents unless the context clearly dictates otherwise. Thus, for example, reference to a quantity of one of a particular element can comprise two or more such elements unless the context indicates otherwise.

Ranges can be expressed herein as from "about" one particular value, and/or to "about" another particular value. When such a range is expressed, another aspect comprises from the one particular value and/or to the other particular value. Similarly, when values are expressed as approximations, by use of the antecedent "about" or substantially," it will be understood that the particular value forms another aspect. It will be further understood that the endpoints of each of the ranges are significant both in relation to the other endpoint, and independently of the other endpoint.

For purposes of the current disclosure, a material property or dimension measuring about X or substantially X on a particular measurement scale measures within a range between X plus an industry-standard upper tolerance for the specified measurement and X minus an industry-standard lower tolerance for the specified measurement. Because tolerances can vary between different materials, processes and between different models, the tolerance for a particular measurement of a particular component can fall within a range of tolerances.

As used herein, the terms "optional" or "optionally" mean that the subsequently described event or circumstance may or may not occur, and that the description comprises instances where said event or circumstance occurs and instances where it does not.

The word "or" as used herein means any one member of a particular list and also comprises any combination of members of that list.

Parts such as mechanical or electrical parts for systems large and small are typically made in a factory using large fixed tooling and shipped to large warehouses for storage. Parts can be "made to order" (MTO) or "build to order" (BTO), in which case by definition production and in some cases even preparation for production (e.g. the purchase of certain raw materials) is not initiated until an order is received and processed by the factory. Such an MTO process, while minimizing or eliminating inventory of excess parts and potentially per-piece cost (or "piece price") if only large orders are accepted or smaller orders are combined, can take days—or more likely weeks or months—to carry out from start to finish.

Parts can also be "made to stock" (MTS), in which case parts are produced based on estimates of future customer needs and then stored in a warehouse or in a store until a customer orders or arrives to purchase a part. Such a MTS process, while minimizing lead time and piece price, can require the setting aside of large amounts of space to hold the inventory produced (and, in any case, will require the setting aside of some space). As typically implemented, both MTO and MTS production systems rely on the factory to fabricate specific parts using its large, fixed tooling and almost exclusively based on predetermined, fixed designs. With either system, one must choose between a shorter lead time and low or no inventory. One cannot have both. In contrast, a mobile manufacturing system such as that disclosed herein can result in shorter lead times and low or no inventory.

In one aspect, a mobile manufacturing system and associated methods, systems, devices, and various apparatuses are disclosed herein. In one aspect, the mobile manufacturing system can comprise a control unit. In other aspects, the mobile manufacturing system can comprise at least a one of a scanner and a manufacturing unit. The mobile manufacturing system can be configured to specify, fabricate, and evaluate a component of a water infrastructure system or other systems onsite, i.e., at a worksite whether the work is being done or at a location proximate to the worksite.

FIG. 1 shows a network diagram for a mobile manufacturing system 90 comprising a mobile manufacturing platform 100. The system 90 can further comprise a server 110, a material storage unit 120, a network 130 (which can be a cloud network or "cloud" in some aspects), a transport device 140, a certification agency 150, and a worksite 160. The server 110 can comprise a database.

As shown, the worksite 160 can comprise a water infrastructure system 50 comprising components such as an original or first component 61 and a replacement or second component 62. The mobile manufacturing platform 100 can comprise or be positioned on or within a vehicle 70, which can be a truck as shown or any other vehicle including one configured to travel by air, water, road, or rail.

In some aspects, the server 110 can be operatively coupled to, for example and without limitation, either the material storage unit 120 or the certification agency 150 or, as shown, both the material storage unit 120 and the certification agency 150—and indirectly to the other elements of the system 90. In some aspects, the material storage unit 120 can be operatively coupled to, for example and without limitation, either the server 110 or the transport device 140 or, as shown, both the server 110 and the transport device 140. In some aspects, the transport device 140 can be operatively coupled to, for example and without limitation, either the material storage unit 120 or the mobile manufacturing platform 100 or, as shown, both the material storage unit 120 and the mobile manufacturing platform 100. As shown, for example and without limitation, the certification agency 150 can be operatively coupled to, for example and without limitation, the server 110 or the mobile manufacturing platform 100. The system 90 or at least a part of the system 90 such as the mobile manufacturing platform 100 can be positioned on or proximate to the worksite 160. Any one or more of the elements of the system 90 can be operatively coupled to or otherwise in communication with, for example and without limitation, the network 130, and through the network 130 to any other element of the system 90.

The server 110 can comprise a computer-readable storage medium (not shown) such as described below. The server 110 also represents any type of networking equipment that has network traffic management responsibilities on or between one or more of the networks 130. The server 110 can comprise firmware (not shown, but see firmware or OS 222 described below) that controls the operation and network traffic management functions of the device. Extensions to the firmware can be implemented by any combination of, for example and without limitation, firmware code modifications, additional software modules, shell scripts, and the like. The firmware can comprise various functions (not shown) for managing network traffic or a scheduler (not shown) for running configuration, maintenance, and other processes at defined times and frequencies.

The computer-readable storage medium can be configured to selectively store data sufficient for defining at least a portion of specifications of a physical component of a system such as, for example and without limitation, the component 61 of a water infrastructure system 50. The server 110 can be further configured to selectively send the data describing the component 61 to and receive the data from the certification agency 150.

The manufacturer or supplier of the components 61, 62 can store design or manufacturing data on the server 110 or on any other device comprising a computer-readable storage medium such as described below. Such data can comprise, for example and without limitation, material type, material strength, component geometry, flow capacity, the existence or non-existence of certain features, tool paths or manufacturing sequences, the existence or non-existence of approvals by the certification agency 150, the applicability and terms of part and/or service warranties, and any conditions or other details corresponding any of the above. The data for each of the components 61, 62 can be developed when each component 61, 62 is initially designed or at any point in time afterwards and can be revised as needed at any point as needed or desired.

The data can be embedded into each of the components 61, 62 by any applicable technology such as, for example and without limitation, radio frequency identification (RFID), and the mobile manufacturing platform 100 can comprise a special reader or other device (not shown) or such capability can be incorporated into any electronic device including a cellular-based device such as a smart phone or electronic tablet. The data can be electronically authenticated by a common digital signature shared by all of the components 61, 62 that are manufactured or certified by, e.g., the manufacturer or the certification agency 150, or by a unique digital signature that contains part number and serial number or similarly unique identifying information. The digital signature can be used to access the data from a database maintained in, for example and without limitation, the server 110 or the network 130.

The data can comprise, for example and without limitation, an expiration date set by the manufacturer, certification agency, or other regulatory body. Similarly to permissions embedded in a typical electronic document, the data embedded in the components 61, 62 can comprise information from the manufacturer or the certification agency 150 on which individuals or entities are authorized by contract or otherwise to install, replace, use, or otherwise handle the components 61, 62. The data can further facilitate charges or credits to an individual or entity for a particular use of the components 61, 62, by, for example and without limitation, simultaneously charging the account of a customer receiving and crediting the account of a serviceperson installing the components 61, 62 for work performed. Through the connection between the server 110 and the network 130, the data can be accessed wirelessly from the network 130 via any device connectable to the network 130 such as the mobile manufacturing platform 100 or elements thereof.

The component 61 of the water infrastructure system 50 can comprise, for example and without limitation, a pipe or pipe segment 51, 52, a pipe fitting, a pipe coupling, a valve, a hydrant, or a leak detection system component. In some aspects, the component 61 can be formed from a rigid material such as, for example and without limitation, a metal such as stainless steel or titanium, a plastic such as acrylonitrile butadiene styrene (ABS), a ceramic material, or any other material as desired. In other aspects, the component 61 can be formed from a resilient material such as a rubber or a rubber-like material. While it is not uncommon for those who inspect and service systems such as the water infrastructure system 50 to carry extra parts for use in making typical repairs involving the replacement of the component 61, the size of some components and the variety and number of components "in the field" generally can make it impractical or expensive to carry one of every variation of the component 61 that a serviceperson might possibly need to replace. This is especially true for industrial systems involving larger components. In addition, some components such as the component 61 can fail not due to natural causes that a manufacturer or user or serviceperson might reasonable foresee (e.g., predictable wear, fatigue, or corrosion) but rather at an inopportune time due to unexpected damage to the water infrastructure system 50 caused by other causes such as, for example and without limitation, an accident involving the water infrastructure system 50, misuse of the water infrastructure system 50, or damage to the system caused by earthquakes, floods, falling trees, or other natural disasters. In other aspects, the component 62 need not replace any pre-existing component, such as when the component 62 is the result of a custom design process and not simply the replacement of a pre-existing part. For example and without limitation, the component 62 can be designed and fabricated to join misaligned pipe segments (e.g., with a coupling, an adapter, or an elbow) in a way that no "off-the-shelf" or standard part could.

Figure 2:
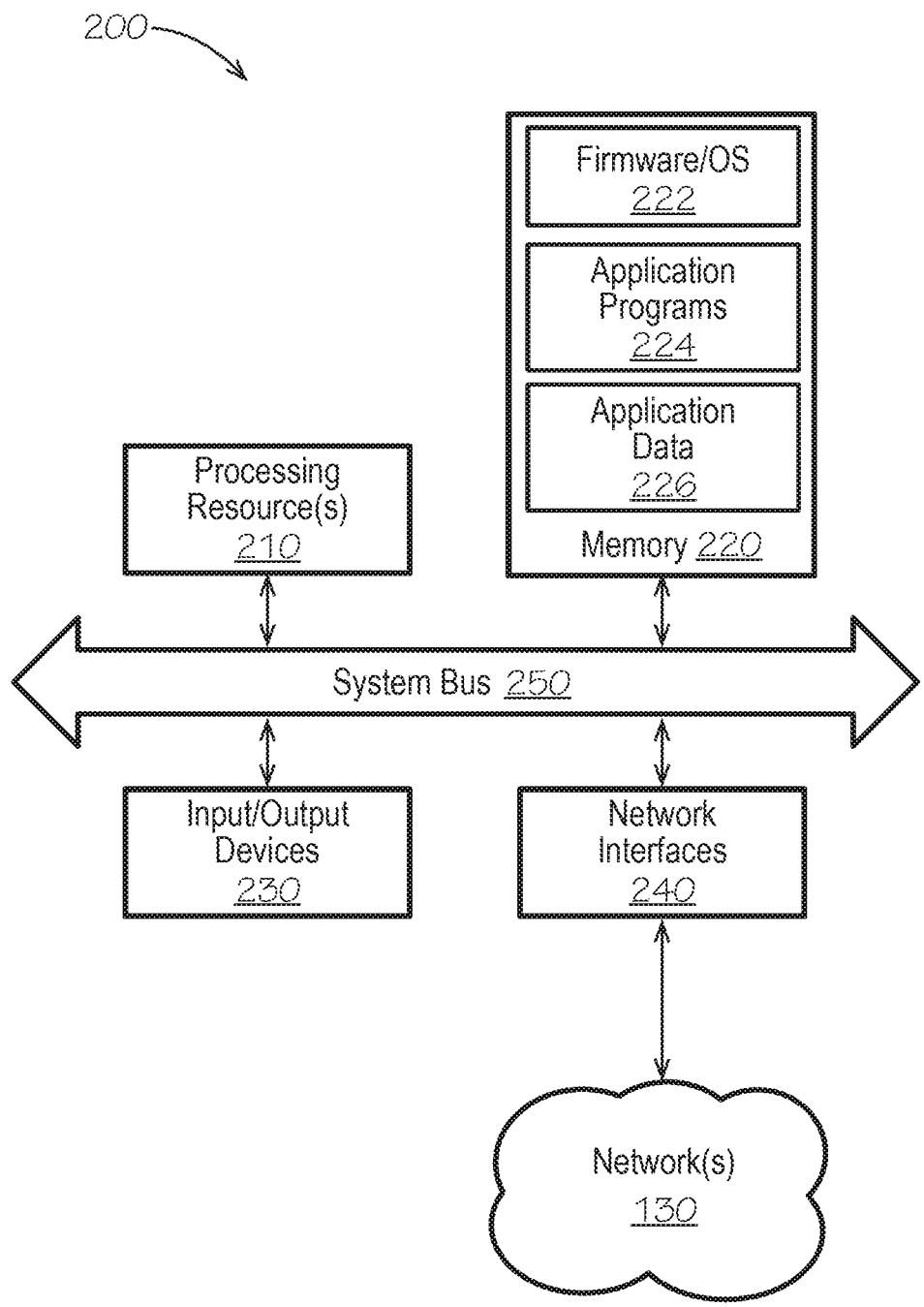
FIG. 2 is a schematic diagram illustrating a computer architecture for network devices, servers, and other computing devices described herein as part of the mobile manufacturing system, in accordance with one aspect of the current disclosure.

FIG. 2 is a schematic or block diagram illustrating various aspects of a computing architecture 200 for networking equipment and other computing devices utilized in the mobile manufacturing system 90. The computing architecture 200 can be utilized in the server 110, the material storage unit 120, the transport device 140, the certification agency 150, the mobile manufacturing platform 100 or any portion thereof, cloud-based servers, or other computer systems described herein or for performing the methods described herein. As shown in this aspect, the computing architecture 200 can comprise processing resource(s) 210 and a memory 220. The computing architecture 200 can further comprise input/output devices 230 and network interfaces 240. The components of the computing architecture 200 can be interconnected and can be made to communicate with each other via a system bus interface or system bus 250 or other suitable communication devices.

The processing resource(s) 210 can comprise, for example and without limitation, one or more general-purpose or specific-purpose processors, microcontrollers, FPGAs, and/or the like for controlling the operations and functions of the server or device. In some implementations, the processing resource(s) 210 can comprise a plurality of processors, computers, servers, or other processing elements for performing different functions within the computing architecture 200. The memory 220 can comprise any combination of volatile and non-volatile memory. For example and without limitation, volatile memory can comprise random access memory ("RAM"), dynamic RAM ("DRAM"), static RAM ("SRAM"), and the like, while non-volatile memory can comprise read only memory ("ROM"), electrically erasable programmable ROM ("EEPROM"), FLASH memory, magnetic storage devices, such as a hard-disk drive ("HDD"), optical storage devices, such as a DVD-ROM drive, and the like. The memory can be configured to store any combination of information, data, instructions, software code, and the like.

In some aspects, the memory 220 can be configured to store a firmware and/or operating system ("OS") 222 for controlling the basic operation of the device or server. The memory 220 can further store application program(s) 224 and application data 226 for performing the specific processes or functions for operating the system 90 as described herein. For example and without limitation, the memory 220 of the server 110 can store various control modules for operating individual elements of the system 90 and for facilitating communication between these individual elements and/or the individual elements inside the mobile manufacturing platform 100. In addition, other modules or services can be stored in one or more memories 220 and run on the same or different computer systems and/or servers.

In addition to the memory 220, the computing architecture 200 can comprise other computer-readable media storing information, data, instructions, software code, etc. It will be appreciated by those skilled in the art that computer-readable media can be any available media that can be accessed by the computing architecture 200 such as, for example and without limitation, computer-readable storage media and communications media. Communications media can comprise, for example and without limitation, transitory signals. Computer-readable storage media can comprise, for example and without limitation, volatile and non-volatile, removable and non-removable storage media implemented in any method or technology for the non-transitory storage of information. For example and without limitation, computer-readable storage media can comprise RAM, ROM, EEPROM, FLASH memory, or other solid-state memory technology, DVD-ROM, BLU-RAY or other optical storage, magnetic cassettes, magnetic tape, magnetic disk storage or other magnetic storage devices and the like. In other aspects, the computing architecture 200 can comprise computer-readable media storing processor-executable instructions that cause the processing resource(s) 210 to perform aspects of the methods 400, 500, 600 described herein in regard to FIGS. 4-6.

The input/output devices 230 can comprise various input mechanisms and output mechanisms. For example, input mechanisms can comprise various data entry devices such as, for example and without limitation, keyboards, keypads, buttons, switches, touch pads, touch screens, cursor control devices, computer mice, stylus-receptive components, voice-activated mechanisms, microphones, cameras, infrared sensors, or other data entry devices. Output mechanisms can comprise various data output devices such as, for example and without limitation, computer monitors, display screens, touch screens, audio output devices, speakers, alarms, notification devices, lights, light emitting diodes, liquid crystal displays, printers, or other data output devices. The input/output devices 230 can also comprise interaction devices configured to receive input and provide output such as, for example and without limitation, dongles, touch screen devices, and other input/output devices, to enable input and/or output communication.

The network interfaces 240 can comprise various devices for interfacing the computing architecture 200 with one or more types of servers, computer systems, and communication systems, such as, for example and without limitation, a network interface adaptor as is known in the art. The network interfaces 240 can comprise devices for communicating between and among the server 110 and the other elements of the system 90 over the network(s) 130, for example.

In some aspects, each component of the computing architecture 200 as shown can comprise multiple components on multiple computer systems of a network. For example, the computing architecture 200 can comprise servers such as, for example and without limitation, application servers, file servers, database servers, web servers, etc., for performing various functions described herein. The servers of the computing architecture 200 can for example be physically separate computer servers or virtual servers hosted in a virtual environment, among other implementations. In further aspects, one or more components of the computing architecture 200 can be combined in a single physical component. For example, the processing resources 210, the memory 220, the network interfaces 240, and the system bus 250 can be combined in a single system-on-chip (SoC) hardware implementation. It will be appreciated that the server 110 and/or other computing resources of the system 90 may not comprise all of the components shown in FIG. 2, may comprise other components that are not explicitly shown in FIG. 2, or may utilize an architecture completely different than that shown in FIG. 2.

Figure 3:
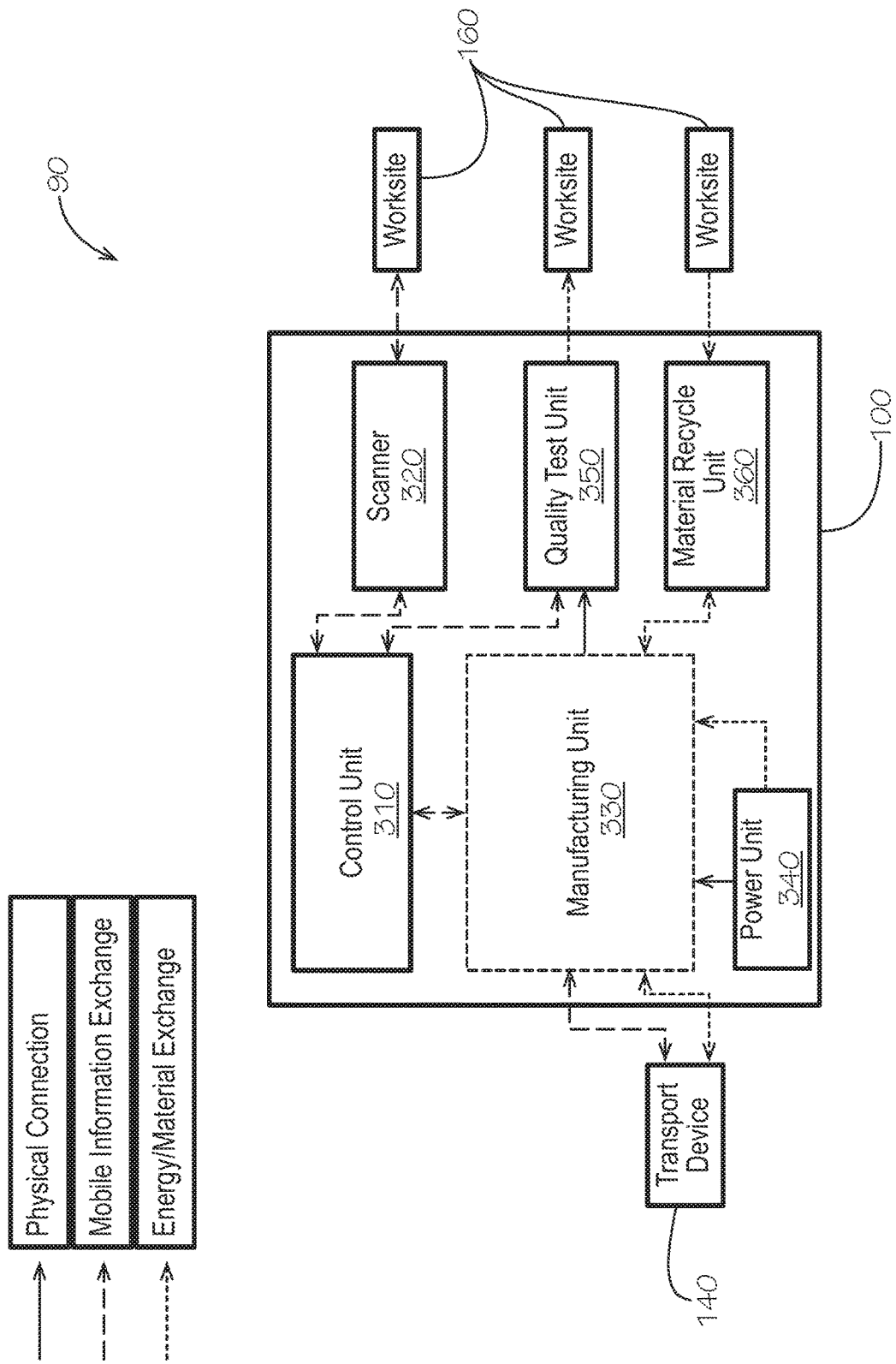
FIG. 3 is a schematic diagram of the mobile manufacturing platform of FIG. 1.

FIG. 3 shows a schematic diagram for the mobile manufacturing platform 100 and select elements of the mobile manufacturing system 90. The mobile manufacturing platform 100 can comprise a control unit 310, a scanner 220, a manufacturing unit 330, a power unit 340, a quality test unit 350, and a material recycle unit 360. While not necessarily part of the mobile manufacturing platform 100, the mobile manufacturing system 90 can again comprise the network 130, the transport device 140, the certification agency 150, and the worksite 160.

Exemplary connections inside the mobile manufacturing platform 100 (as shown in FIG. 3) and between each of the mobile manufacturing platform 100, the server 110, the material storage unit 120, the network 130, the transport device 140, the certification agency 150, and the worksite 160 are shown in FIG. 3 using one of three different line types. A solid line represents a physical connection, a coarse dashed line represents the exchange of information, and a fine dashed line represents the exchange of energy or material. What is shown in one aspect in any one of FIGS. 1-3 as one particular line type, for example a solid line, in other aspects can be shown in one of the other two line types. As shown, more than one type of exchange can occur—for example, both information and material in several exchanges as shown in FIG. 2.

Referring again to FIG. 1, the material storage unit 120 can be configured to store at least one of raw materials (not shown), partially fabricated parts (not shown), and fabricated parts (not shown) for use by the system 90. Raw materials can comprise, for example and without limitation, materials for use by the mobile manufacturing platform 100 including the manufacturing unit 330 for fabricating or evaluating components built or to be built by the system 90. More specifically, raw materials can comprise, for example and without limitation, a resin or a metal in filament or powder form for use by the aforementioned three-dimensional printer to fabricate parts in an additive manufacturing process; or materials such as cast or molded metal or plastic used by the manufacturing unit 330 to fabricate parts in a subtractive manufacturing process. In yet other aspects, materials such as a pelletized resin can be used in a molding process or discrete strips or layers of materials such as carbon fiber or fiberglass can be used in a glass-laying process. Partially fabricated parts can comprise components having a generic shape that can be further processed (by machining, for example) to create a component having a custom shape for a particular application. Fabricated parts can comprise complete, finished parts that are ready for installation as-is in a system such as the water infrastructure system 50.

Any one of the raw material, the partially fabricated parts, and the fabricated parts can be supplied by the original manufacturer or an agent or designated vendor thereof. Such as, for example and without limitation, in the case of filament for the three-dimensional printer, the raw material filament can be delivered in cartridges and authenticated as manufactured or certified by the original manufacturer of the components 61, 62. The raw material, the partially fabricated parts, and the fabricated parts can optionally be stored on or in the vehicle 70 as space is available.

The network 130 can be a cloud computing system, which can be a system of data storage, processing, or transmission services hosted on the Internet. The network(s) 130 can represent local area networks (LANs), wide area network (WANs), and/or other data, communication, or telecommunication networks that collectively make up the Internet. In further aspects, any network(s) 130 that support the TCP/IP protocol may be utilized. For example, the server 110 may represent an Internet router designed for an environment based on popular SoC hardware implementations. In further aspects, the server 110 may represent an enterprise gateway, a wireless access point, a smart network switch, or the like.

The transport device 140 can be configured to transport the at least one of the raw materials, the partially fabricated parts, and the fabricated parts from the material storage unit to the worksite. The transport device 140 can be a vehicle other than the vehicle 70 able to carry a payload over a distance from the material storage unit 120 to the mobile manufacturing platform 100. A transport device 140 can comprise, for example and without limitation, a truck, any devices, systems, and methods used a courier service, or an unmanned aerial vehicle (UAV), i.e., a drone.

The certification agency 150 can comprise a server configured to hold information or collect information about engineered products such as a component of the aforementioned water infrastructure system. The certification agency 150 can be, for example and without limitation, the National Sanitation Foundation (associated with the "NSF" certification mark), Underwriters Laboratories (associated with the "UL" certification mark), or Intertek (associated with the "ETL" certification mark) and the server for the certification agency 150 can be configured to receive data such as the aforementioned data related to the fabrication of the component and grant certification or approval based on predetermined agency requirements that can be shown to have been met based on the data.

In some aspects, as shown in FIG. 3, the network 130 can be operatively coupled to, for example and without limitation, the control unit 310 of the mobile manufacturing platform 100—and indirectly to the other elements of the mobile manufacturing platform 100 and the system 90. In some aspects, the transport device 140 can be operatively coupled to, for example and without limitation, the manufacturing unit 330 of the mobile manufacturing platform 100. As shown, for example and without limitation, the certification agency 150 can be operatively coupled to, for example and without limitation, the control unit 310 of the mobile manufacturing platform 100. The system 90 or any one or more of the system 90 such as the control unit 310, the scanner 320, the manufacturing unit 330, the power unit 340, the quality test unit 350, or the material recycle unit 360 can be positioned on or proximate to the worksite 160.

Inside the mobile manufacturing platform 100, the control unit 310 can be operatively coupled to, for example and without limitation, the scanner 320, the manufacturing unit 330, or the quality test unit 350. The manufacturing unit 330 can be operatively coupled to the power unit 340, the quality test unit 350, or the material recycle unit 360.

The control unit 310 can be configured for ready portable transport via the vehicle 70 from a storage site to the worksite 170 located remotely from the storage site and then back to the storage site. "Portable transport" means that the control unit (or other component of the system 90) can be moved from one location to another. "Ready portable transport" means that it is designed to be moved and used in multiple locations on a regular or rotating basis such as, for example and without limitation, on or inside a truck or other vehicle 70. "Portable transport" does not include a system that requires extensive bolting and unbolting to a fixed location move it, and "readily portable" does not include a system that must be loaded and unloaded from the truck or vehicle each time.

The control unit 310 can be configured to operatively couple to the server 110. More specifically, the control unit 310, indirectly through the network 130 or directly can send data to or receive data from the server. The control unit 310 can further be configured to control any of, for example and without limitation, the scanner 320, the manufacturing unit 330, and the quality test unit 350.

The mobile manufacturing platform 100 can comprise a scanner 320, which can be three-dimensional scanner operatively coupled to the control unit 310. The scanner 320 can be configured for ready portable transport via the vehicle 70 to the worksite 160. The scanner 320 can be configured to convert the geometry of the first component 61 of the water infrastructure system 50 into electronic data based on a physical scan of the first component 61. Additionally, a one of the scanner 320 and the control unit 310 can comprise a converter or converter module (not shown) configured to convert the data into a three-dimensional solid model of the first component 61.

The scanner 320 can comprise solid-state electronics. The scanner 320 can comprise a movable scanning head. The scanner 320 can be powered by a battery or by the power unit 340. The scanner 320 can be configured to communicate wirelessly with any other component of the system 90 including, for example and without limitation, the network 130, the control unit 310, and the manufacturing unit 330.

The scanner 320 can be any device configured to "read" and "record" and thereby generate data based on the physical geometry of the components 61, 62. The scanner 320 can comprise scanning technologies such as, for example and without limitation, an optical scanning technology (e.g., using a laser), an X-ray scanning technology, or an ultrasonic scanning technology. The output of any of these scanning processes can be a "point cloud," from which the converter, can create the three-dimensional solid model, or multiple point clouds are other images, taken from multiple views as appropriate, from which the converter can effectively reconstruct the shape of the component 61, 62, the space or gap to be filled, or, for example and without limitation, the pipes 51, 52 (shown in FIG. 1) to be joined. The converter can comprise software (i.e., a module or modules implementing a set of instructions) running on, for example and without limitation, the network 130, the control unit 310, or the scanner 320.

The generated solid model can be further processed by this or other software operating on or in the control unit 310, the scanner 320, the manufacturing unit 330, or some other element of the mobile manufacturing platform 100 to incorporate custom design offsets and transition couplings or adaptors (e.g., when pipe segments needing to be joined are misaligned). The software and any device on which it operates can further generate designs for custom valves and other components having, e.g., unique ends to match inlet and outlet pipes of different sizes, custom geometry such as a bypass on a gate valve, and additional features such as sensors or other electronic equipment. Moreover, the control unit 310, the scanner 320, the manufacturing unit 330, or some other element of the mobile manufacturing platform 100 can be powered by an artificial intelligence (AI) engine as will be described below.

The scanner 320 or some other element of the mobile manufacturing platform 100 can further comprise a spectrometer (not shown) such as, for example and without limitation, an X-ray mass spectrometer able to identify a specification of a material forming the first component 61 by measuring and analyzing, for example and without limitation, the material's component elements.

In some aspects, the manufacturing unit 330 can be configured to fabricate the second component 62 of the water infrastructure system 50 using the specifications of the first component 61 stored on the computer-readable storage medium of the server 110. In other aspects, the manufacturing unit 330 can be configured to fabricate the second component 62 of the water infrastructure system 50 without the specifications of the first component 61, for example and without limitation, when an entirely new branch or component is added to the water infrastructure system 50. The manufacturing unit 330 can be operatively coupled to the control unit 310 and configured for ready portable transport via the vehicle 70 to the worksite 160. The manufacturing unit 330 can be configured to fabricate the second component 62 of the water infrastructure system 50 using an automated manufacturing process based on the solid model of the first component 61.

In some aspects, the manufacturing unit 330 can comprise an automated manufacturing device using an additive manufacturing process such as, for example and without limitation, the three-dimensional printer. In an additive manufacturing process, material is generally built up or added in increments to fabricate each component through a process such as, for example and without limitation, sand printing, plastic printing, or weld printing. In yet other aspects, the manufacturing unit 330 can comprise a hybrid manufacturing system comprising both additive and subtractive manufacturing processes. The raw material used by such a printer can be, for example and without limitation, a light-cure resin or a powder. In other aspects, the manufacturing unit 330 can comprise an automated manufacturing device using a subtractive manufacturing process such as, for example and without limitation, a vertical machining center or a lathe. In a subtractive manufacturing process, material is generally cut away or otherwise removed in increments to fabricate components. In yet other aspects, a manufacturing process utilized by the manufacturing unit 330 involves neither the addition or removal of material per se, such as when a component 61, 62 is formed through a molding process by inserting a molten material into a cavity of a mold. For example and without limitation, each of the components 61, 62 can be fabricated as a monolithic casting or portions of the components 61, 62 can be fabricated as monolithic castings and can be assembled together or otherwise processed or machined to create the finished component 61, 62. Each monolithic casting can be formed from a single material in a single casting operation and without any welds or mechanical connections such as threading, flanges, fasteners, interference fits, adhesives, brazing, soldering, or other mechanical methods of connection except as desired.

Additive manufacturing refers to a process in which a three-dimensional (3D) object can be formed by depositing or bonding successive layers of material to previously formed layers of material. Additive manufacturing can comprise different types of processes such as a deposition, a light polymerization, a powder bed, or a lamination process. For example, in a deposition process, material can be selectively deposited according to a cross-section of the 3D object corresponding to that layer. The material can be deposited through methods such as extruding a material in a molten state, which can fuse to the previous layer or depositing material in the form of a wire or granule while applying an energy source such as an electrical current or laser to fuse the material to the previous layer. The material is only applied to areas corresponding to the cross-section of the layer. Deposition processes can comprise, for example and without limitation, fused deposition modeling, robocasting, directed energy deposition, electron beam freeform fabrication, 3D printer extrusion, and material jet printing.

By contrast, in a powder bed process, a layer of loose granular material can be evenly applied in a bed or a job box, and areas of the layer corresponding to the cross-section of the 3D object for that layer can be selectively treated to fuse or bind the material together. In some powder bed processes, a glue or binder can be selectively sprayed on the layer of granular material which binds the loose granular material together to form the cross-section. In some powder bed processes, an energy source such as a laser, an electron beam, or an electrical current can be selectively applied to melt and sinter the granular material corresponding to the cross-section of the 3D object. Successive layers can be sintered or bound to previous layers, and the remaining loose granular material can be removed leaving the 3D object behind upon completion. Powder bed processes can comprise, for example and without limitation, binder jetting, 3D sand printing, direct metal laser sintering, electron beam melting, selective heat sintering, and selective laser melting, which will be described in more detail below.

Light polymerization processes can be similar to powder bed processes with the difference being that the material is often deposited as a liquid, such as a polymer resin in a bath or a vat instead of a job box. The material can be selectively treated with an energy source such as a light source, a heat source, or a laser corresponding to the cross-section for the layer. The energy source can cause the material to solidify, thereby forming the cross-section of the 3D object for the layer. Light polymerization processes can comprise, for example and without limitation, stereolithography and digital light processing.

Lamination processes supply material in the form of a foil or a film, often fed from a roll, which can be treated with an adhesive or bonded by other means. The material is fed over a platform upon which the 3D object is built. A mechanical means, such as a blade, or an energy source, such as a laser, can cut out the first layer corresponding to the first cross-section of the 3D model from the material and deposits the material on the platform. The platform can then lower and a new portion of the foil or film can be fed over the platform, and a successive layer can be cut out corresponding to a second cross-section of the 3D object. The successive layer can then be bonded to the previous layer by the adhesive. Lamination processes can comprise, for example and without limitation, laminated object manufacturing and ultrasonic consolidation.

When forming the mold in the 3D sand printing process, which can incorporate both additive and non-additive processes, a first arm of a 3D sand printing machine can deposit a thin, substantially planar layer of sand in the job box. The layer of sand can have a layer thickness. A second arm can traverse over the layer of sand and selectively spray a binder on the layer of sand corresponding to the cross-section of the 3D object for a first layer. Areas of the sand sprayed by the binder can cement together while areas not sprayed by the binder can remain loose and granular. The layer can be selectively sprayed with the binder on the layer of sand corresponding to the cross-section of the mold for the first layer at a first mold height. The cross-sections of the mold can be formed such that solid portions of the component 61, 62 can correspond to voids in the mold, and openings or cavities in the component 61, 62 can correspond to solid portions of the mold.

The job box can then be lowered by an incremental distance equal to the layer thickness, and the first arm can then deposit a successive planar layer of sand. The second arm can then traverse over the successive layer of sand, and can selectively spray the binder on the successive layer of sand corresponding to a cross-section of the mold of a second layer at a second mold height which can cement the sprayed areas and can bond the sprayed areas of the second layer to the sprayed areas of the first layer. The process can repeat, alternatively depositing the substantially planar layers of sand and then selectively spraying the binder on the layer of sand until the mold has reached its full height. The mold can be built up from the bottom layer by layer until the mold is fully formed.

Once the mold is fully formed, the sand that has been treated by the binder becomes the mold while the untreated sand remains loose and granular and can be shaken, vacuumed, blown, or brushed away. In some aspects, the mold can comprise multiple subcomponents which can be glued or mechanically connected to assemble the mold. The mold can define vents to allow air to escape when molten material is poured into the mold. The mold can define a component mold cavity formed complimentary to a shape of the component 61, 62.

Upon assembling the mold, a molten material, such as molten metal, can be poured into the mold. After the molten material has solidified, the component 61, 62 can be removed from the mold. Because the mold is made of sand, it can be destroyed to remove the component 61, 62 and any mold cores that are present. The mold can be broken up by mechanical means such as with a hammer, chisel, or drill, by vibrations such as with ultrasonic waves, or by spraying with water such as from a high-pressure source. In some aspects, the binder can be water-soluble. In other aspects, the mold can be re-used. In other aspects, the component 61, 62 can be formed by 3D printing the respective component 61, 62 from a suitable material directly rather than 3D printing the mold as a tool for use in casting the component 61, 62.

In other aspects, the component 61, 62 can be formed by an investment casting process. A master pattern of the component 61, 62 can be formed, such as by an additive manufacturing process. The master pattern can be substantially identical in shape and size to the component 61, 62 or a subcomponent thereof. The master pattern can be used to cast a master mold or a master die around the master pattern, thereby producing a master mold cavity shaped complimentary to the component 61, 62 or a subcomponent thereof. So-called "wax patterns" can then be cast within the master mold cavity from materials such as plastic, wax, or foam. The wax patterns can also be substantially identical in shape and size to the component 61, 62 or a subcomponent thereof. In some investment casting processes, individual wax pattern subcomponents can be assembled to form an assembled wax pattern which can be substantially identical in shape and size to the component 61, 62.

A ceramic mold, or an investment, can be formed by applying and curing coats of ceramic refractory material to the wax pattern. Once the investment has cured, the wax pattern can then be melted or vaporized out of the investment, leaving an open investment cavity formed complimentary to the component 61, 62. The component 61, 62 can then be cast in the investment by pouring molten material into the open investment casting. Upon solidification of the molten material, the component 61, 62 can be divested or removed from the investment. Operations such as media blasting, hammering, vibration, or water jetting can be used to divest the component 61, 62 from the investment. Alternatively, an additive manufacturing process could be used to form the individual wax patterns rather than the master pattern.

Either one of the scanner 320 and the manufacturing unit 330 or both can be configured to "park" or securely hold in place certain components such as spindles, scanning heads, or print heads, which can be more sensitive to vibration encountered during movement of the vehicle 70 comprising the mobile manufacturing platform 100. A "parking" process can secure such components of the scanner 320 or the manufacturing unit 330 for transportation. The scanner 320 or the manufacturing unit 330 can then undergo an "unparking" and calibration process when the mobile manufacturing platform 100 is onsite at the worksite 160. The scanner 320, the manufacturing unit 330, or any other element of the mobile manufacturing platform 100 can be mounted on an anti-vibration shock-dampening system and otherwise configured for mobile transport across air, sea, and land, including across rough terrain.

The mobile manufacturing platform 100 can further comprise a quality test unit 350. The quality test unit 350 can be operatively coupled to the control unit and configured to perform testing on the second component 62 and on "dog bone" samples (not shown) of a batch of a material used to fabricate the second component 62. The dog bone sample is sometimes so named because it resembles a dog bone with two wide ends joined by a narrower central section. The two ends of the sample to be tested are typically made wider to be able to be gripped tight during testing and withstand any loads encountered during the test, and the central section is typically made smaller or narrow so as to predictably fail during the test, the central section being the area of smallest cross-section and therefore the weakest point.

The quality test unit 350 can comprise a tensile test unit (not shown), which can be configured to perform tensile testing on the dog bone samples of the batch of a material used to fabricate the second component 62. More specifically, the manufacturing unit 330 can print a dog bone sample corresponding to each of the three axes, and the tensile test unit of the quality test unit 350 can test each sample to verify the strength of the material in each of three axes as formed using the manufacturing unit 330. Similarly, air or nitrogen or another fluid can be used to leak test or pressure test valves and pressure vessels fabricated with the manufacturing unit 330. In yet another aspect, any other kind of testing such as, for example and without limitation, non-destructive testing (NDT) to inspect for cracks and other defects, hardness testing to evaluate material hardness, and surface finish testing to evaluate surface roughness can be performed. Each set of data gathered from the testing, which can be called quality assurance (QA) data, can be stored on the control unit 110, the network 130, the server 110, the digital signature associated with the component 62, or some other element of the mobile manufacturing platform 100 or the mobile manufacturing system 90. The QA data can be stored for a variety of purposes such as, for example and without limitation, warranty confirmation and claims, insurance confirmation and claims, and other purposes requiring historical documentation.

The mobile manufacturing platform 100 can further comprise a material recycle unit 360. The material recycle unit 360 can be operatively coupled to the manufacturing unit and configured to receive and repurpose by various methods such as, for example and without limitation, crushing, melting, grinding, mixing, purifying, separating, pelletizing, and extruding. In some aspects, a resin material recovered from the first component 61 can, for example and without limitation, be crushed, ground, melted, purified, and extruded into new filament for use in fabricating the second component 62 using the manufacturing unit 330. In other aspects, a metallic material recovered from the first component 61 can, for example and without limitation, be crushed and ground into powder for use in fabricating the second component 62 using the manufacturing unit 330.

The mobile manufacturing platform 100 can further comprise a power unit 340, which can be configured to power at least one of the control unit 310, the scanner 320, the manufacturing unit 330, the quality test unit 350, and the material recycle unit 360. The power unit 340 can comprise a power source comprising at least one of a battery (not shown) and a generator (not shown). Where a battery is used, the battery can be a rechargeable battery. The mobile manufacturing platform 100 can be certified by Underwriter's Laboratories (UL) or similar certification organizations (e.g., Intertek/ETL and NSF) against applicable electrical safety and other standards and can also be certified against ingress protection (IP) and other industry standards.

A method of manufacturing the second component can comprise carrying a mobile manufacturing platform 100 with a vehicle 70 from a storage site (not shown), which can be located anywhere, to a worksite 160 located remotely from the storage site. The method can further comprise sending the solid model of the first component 61 or an equivalent thereof to the manufacturing unit. An exemplary equivalent of the solid model of the first component 61 can be data such as the aforementioned point cloud from a three-dimensional scanner such as the scanner 320 that can be converted into the solid model. Another exemplary equivalent of the solid model of the first component 61 can be an identifier such as a drawing number or file name or model number that points to the solid model or the location in which it the solid model is stored. The method can further comprise fabricating a second component 62 using an automated manufacturing process based on the solid model of the first component 61 saved on the computer-readable storage medium operatively coupled to the control unit 310.

The method can further comprise scanning into electronic data with the scanner 320 the three-dimensional geometry of the first component 61. The method can further comprise converting the data into a three-dimensional solid model of the first component 61 using the converter. The method can further comprise sending the data from the control unit 310 to the server 110 and storing the data on the computer-readable storage medium. The method can further comprise sending the data to or receiving data from the certification agency 150.

The method can further comprise storing at least one of raw materials, partially fabricated parts, and fabricated parts in a material storage unit 120 located separately from the worksite 160 and the vehicle 70; and transporting the at least one of the raw materials, the partially fabricated parts, and the fabricated parts from the material storage unit 120 to the worksite 160. The method can further comprise fabricating the second component 62 with the aforementioned three-dimensional printer.

The method of using the mobile manufacturing platform 100 and particularly the quality test unit 350 can further comprise fabricating a dog bone sample—in any one of multiple orientations or axes where the strength may vary between orientations based on the manufacturing process—from a batch of a material used to fabricate the second component 62; performing tensile testing on the dog bone sample; comparing a tensile strength of the dog bone sample with a reference strength of the material used to fabricate the second component; and alerting a user of the system as to whether the tensile strength of the dog bone sample is within an acceptable range about the reference strength of the material.

The method can further comprise receiving the first component 61 for disposal within the material recycling unit; and converting the first component 61 into a recyclable form. The can further comprise tagging the second component 62 with a digital signature that provides information about the second component 62. The method can further comprise scanning the first component 61 with the aforementioned spectrometer to identify a specification of a material forming the first component 61.

Figure 4:
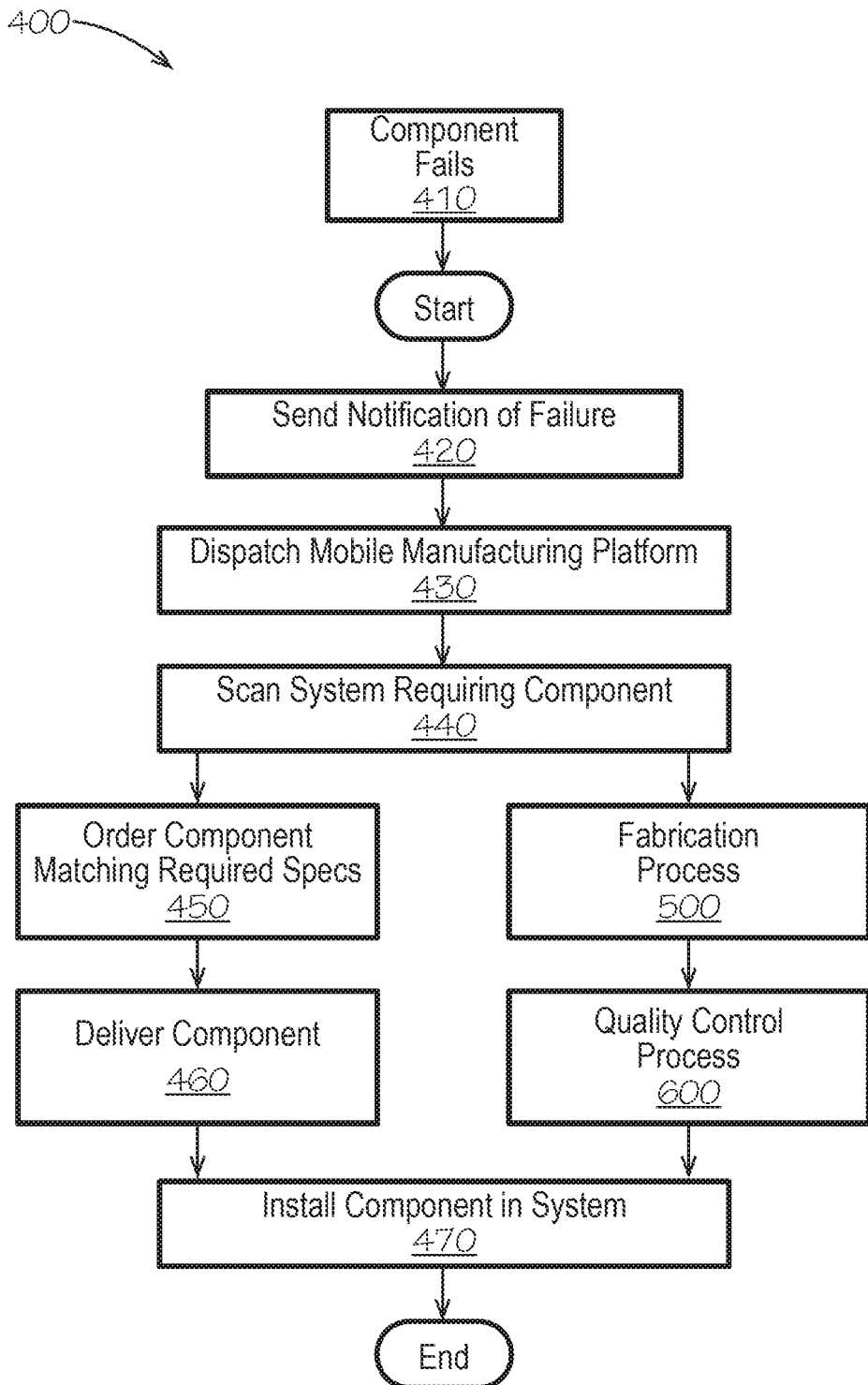
FIG. 4 is a flowchart describing a process for repairing a water infrastructure system using the mobile manufacturing system of FIG. 1.

As shown in FIG. 4 (and as will be described below with respect to FIGS. 7-10), a method 400 for repairing (or otherwise modifying) a system such as the water infrastructure system 50 using the system 90 can comprise steps 410 through 470. A step 410 can comprise failure of the component 61 at issue (or realization of a need to design and/or install a new component), at which time the process for repair can be initiated. A step 420 can comprise a technician, a third party, or the water infrastructure system 50 itself sending notification of failure of the component. A step 430 can comprise dispatching a mobile manufacturing platform 100 to the worksite 160 at which the component 61 is located. A step 440 can comprise three-dimensionally scanning the component 61 or the system 90 requiring the component 62 with the scanner 320. The component 62 can then, for example and without limitation, be fabricated and transported from a remote location (i.e., not at the worksite 160) based on the data gathered from the scanning process or can be fabricated and/or evaluated onsite at the worksite 160.

When the component 62 is fabricated and transported from a remote location, a step 450 can comprise matching the data gathered at the worksite to a component 62 matching the required specifications and ordering the component 62. In another aspect, without a need for scanning the geometry of the component 61, a chip or tag (e.g., using RFID technology) can be located in the component 61 and the chip or tag containing model number information, serial number information, or other information can be directly obtained. Such identifying information can be used to identify the geometry for the component 62 in the server 110 or an already fabricated component 62. A step 460 can comprise delivering the component 62, e.g., by the transport device 140. When the component 62 is fabricated onsite, a method or process 500 (i.e., the Fabrication Process) can comprise fabricating the component 62 and a method or process 600 (i.e., the Quality Control Process) can comprise evaluating the fabricated component 62. Finally, a step 470 can comprise physically installing the second component 62 in the water infrastructure system 50 (or other relevant system).

Figure 5:
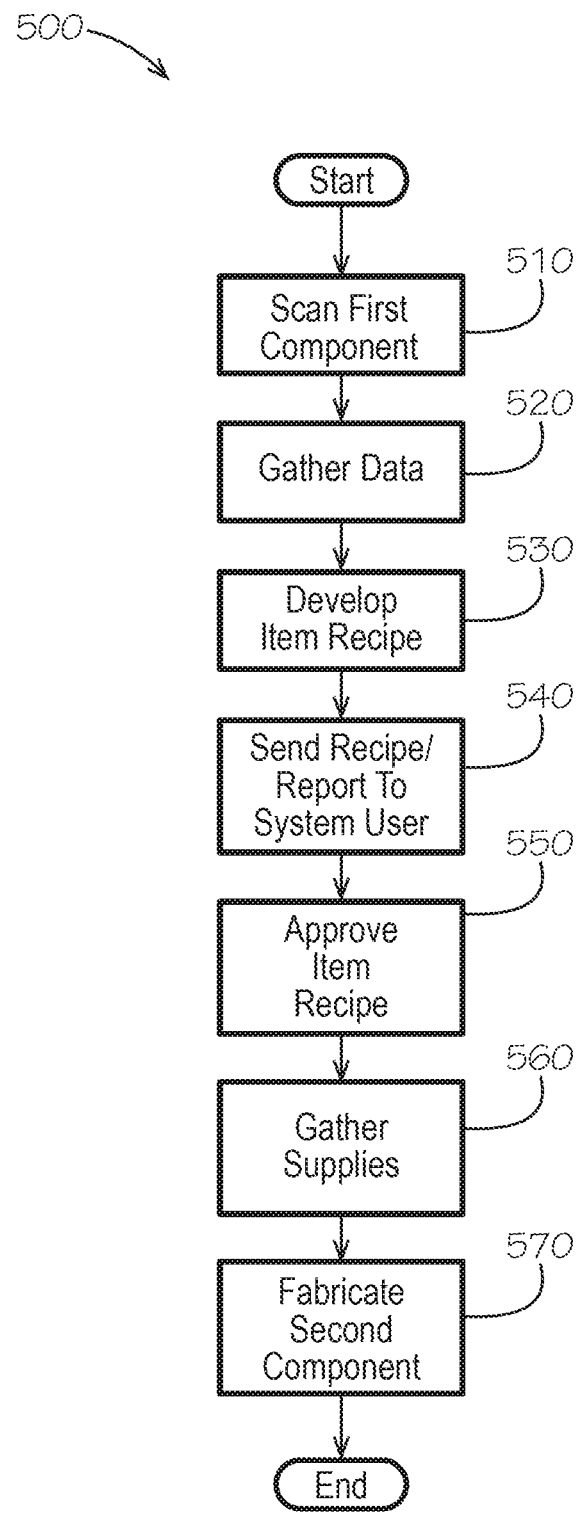
FIG. 5 is a flowchart describing a process for fabricating an object using the mobile manufacturing system of FIG. 1.
Figure 6:
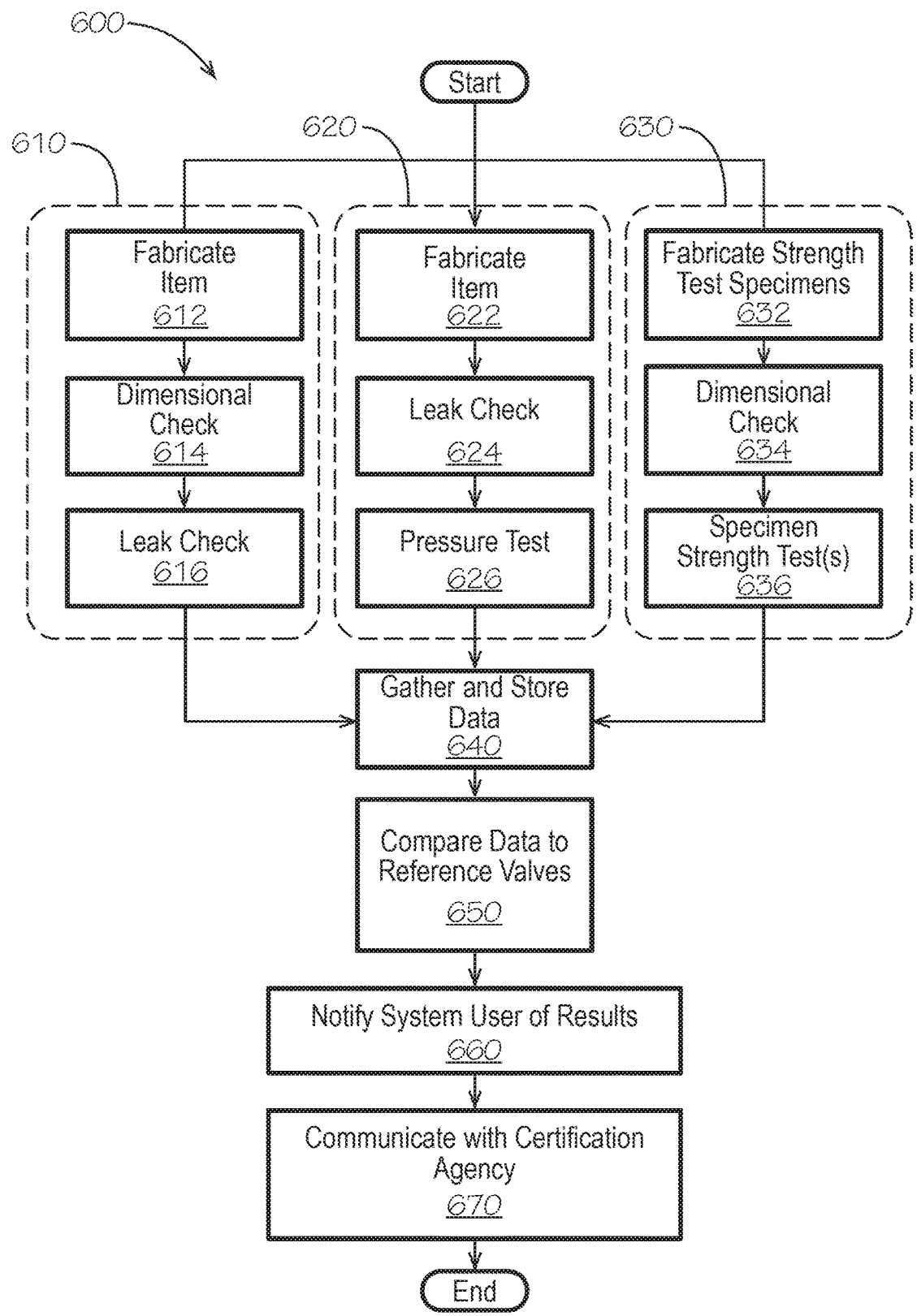
FIG. 6 is a flowchart describing a process for evaluating the properties of an object, including an object that has been fabricated using the mobile manufacturing system of FIG. 1.
Figure 7:
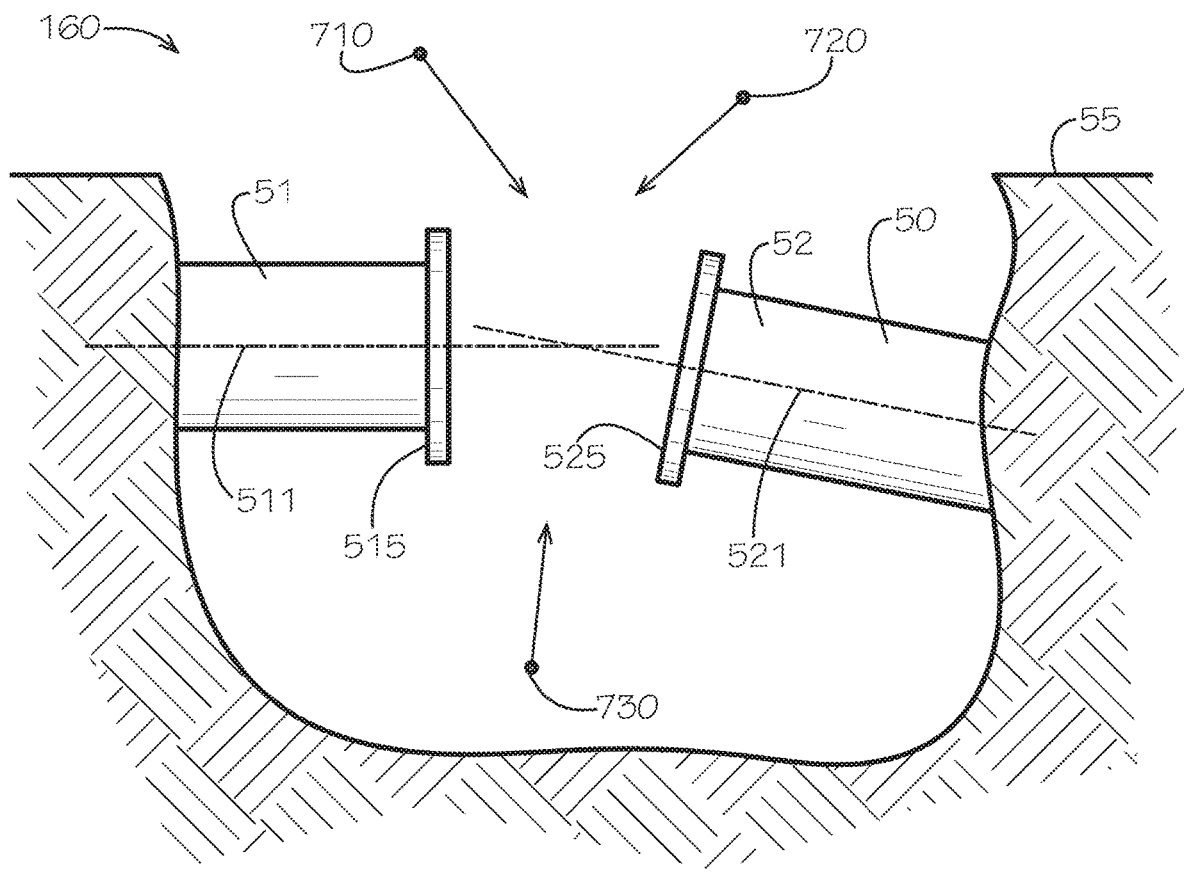
FIG. 7 is a side view of a water infrastructure system comprising two misaligned pipes and a space therebetween, in accordance with one aspect of the current disclosure and in a condition for being three-dimensionally scanned.

As shown in FIG. 5, the method 500 for fabricating a component such as the second component 62 can comprise steps 510 through 570. In some aspects, a step 510 can comprise scanning the first component 61 with the scanner 320. In other aspects, the first component 61 need not be scanned but rather a gap between the two pipes 51, 52 as shown in FIG. 7), which may or may not be filled by a standard or "off-the-shelf" component. A step 520 can comprise gathering data on the first component 61 from the scanner 320. A step 530 can comprise developing an item recipe for the second component 62. A step 540 can comprise sending the recipe and/or a report to a user of the system 90. A step 550 can comprise the user approving the item recipe. A step 560 can comprise gathering supplies required to fabricate the second component 62. Finally, a step 570 can comprise physically fabricating the second component 62.

The aforementioned item recipe, which can be saved inside the control unit 310, can comprise a variety of pieces of information. More specifically, the item recipe can comprise, for example and without limitation, the manufacturing method, the material specification, the material source, the three-dimensional geometry of the component, the manufacturing timelines, or other types of data described above. The manufacturing method portion of the item recipe can comprise information on whether the second component 62 is to be made at the worksite 160 or elsewhere, whether the manufacturing method is to be an additive or subtractive process, and whether one machine or another within the manufacturing unit 330 is to be used to fabricate the second component 62. The material specification portion of the item recipe can comprise information on the color or strength of the material or on specific properties of the desired material for a particular project. The manufacturing timeline portion of the item recipe can comprise information on the time for processing, fabricating, curing, testing, and checking for a particular project.

The method 600 for evaluating a second component 62 can comprise steps 610 through 670. A first step can comprise testing the second component 62 according to one of a plurality of test recipes 610, 620, 630. A step 640 can comprise gathering and storing the data resulting from the testing. A step 650 can comprise comparing the data to reference values. A step 660 can comprise notifying a user of the system of the results. A step 670 can comprise communicating the results to or otherwise communicating with the certification agency 150.

The test recipe 610 can comprise steps 612 through 616. A step 612 can comprise fabricating an item such as the second component 62. A step 614 can comprise performing a dimensional check on the item. A step 616 can comprise performing a leak check on the second component 62. The leak check can be a non-destructive test that pressurizes the second component 62 to a pressure equaling the design pressure, which ensures that the second component 62 can withstand the design pressure of the second component 62, i.e., the pressure that the second component 62 is designed to withstand under use.

The test recipe 620 can comprise steps 622 through 626. A step 622 can comprise fabricating an item such as the second component 62. A step 624 can comprise performing the aforementioned leak test on the second component 62 to provide baseline data. A step 626 can comprise performing a pressure test on the second component 62. The pressure test can be a burst test that pressurizes the second component 62 to a pressure equaling several times the design pressure (including, e.g., a safety factor), which ensures that the second component 62 can withstand the intended burst pressure of the second component 62, i.e., the pressure that the second component 62 is designed to withstand before failure or the pressure at which the second component 62 is designed to fail.

The test recipe 630 can comprise steps 632 through 636. A step 632 can comprise fabricating strength test specimens such as the aforementioned dog bone samples. A step 634 can comprise performing a dimension check on the strength test specimens. A step 636 can comprise performing specimen strength tests on the strength test specimens.

A variety of circumstances can lead to a need for onsite scanning, fabrication, evaluation, and/or other processing of a component 62 using the system 90. For example and without limitation, a technician responsible for all or portions of the water infrastructure system 50, such as a utility company employee or a third party monitoring or service company employee, can locate and discover a need to replace a broken fitting such as the component 61. The technician can then contact a supplier of the component 61 or other fittings of that type, and the supplier can send the mobile manufacturing platform 100 to the worksite 160. An operator of the mobile manufacturing platform 100, having already identified the fitting and noting that the installation is a standard installation, can download the design specifications for the component 61 already saved on the server 110 from the server 110 to the control unit 310 via the network 130. The operator can then fabricate the new replacement fitting, which can be the component 62, using a 3D printer of the manufacturing unit 330 of the mobile manufacturing platform 100. The operator can evaluate and verify the strength of the material and the process used to fabricate the replacement fitting by using the quality test unit 350 and, for example and without limitation, the methods described herein.

In other aspects, for example and without limitation, a valve may need to be built, in which case a different 3D printer of the manufacturing unit 330 using a different additive manufacturing process can be used to fabricate a valve body and a bonnet of the valve, and a gate and a stem of the valve can be delivered by a car and the fasteners used to assemble the valve can be delivered by drone.

As another example and an illustration of the process for onsite scanning, fabrication, and installation of a component 62, a pipe elbow can fail at a water pumping station. The mobile manufacturing platform 100 can be dispatched to the worksite 160 and put to work scanning the pipes 51, 52 and manufacturing a suitable replacement component 62. FIGS. 7-10 show such the water infrastructure system 50 of such a case comprising two misaligned pipes 51, 52 (separately defining misaligned axes 511, 521, respectively) that need to be joined with a new component 62. The pipes 51, 52 are surrounded by earth 55.

FIG. 7 shows the water infrastructure system 50, after the earth 55 is cleared to provide access to the pipes 51, 52, in a condition for being three-dimensionally scanned by the scanner 320 from scanning positions 710, 720, 730. The pipes 51, 52 can be marked or simply cleaned to facilitate accurate identification in the scanned data of each of a plurality of holes 518, 528 in facing flanges 515, 525, respectively, on each pipe 51, 52. The scanner 320 can comprise any available scanning device and can mount on a stand to fix its location during the scanning process. For example and without limitation, the scanner 320 can comprise equipment such as a FAROblu Laser Line Probe HD available from FARO Technologies, Inc. of Lake Mary, Fla.; a Structured Light Scanner Pro S3 3D scanner available from HP Inc. of Palo Alto, Calif.; or a HandyScan 3D scanner available from Creoform Inc. of Levis, Quebec, Canada. The scanner 320 can utilize a scanning technology such as, for example, structured light, photogrammetry, and laser triangulation. The scanner 320 can comprise or be configured to convert or process the collected data using or in cooperation with software such as, for example and without limitation, Geomagic Solutions from 3D Systems of Rock Hill, S.C.; Pro/Engineer from PTC Inc. of Needham, Mass., and Metrolog X4 from Metrologic Group S.A.S. of Meylan, France.

Figure 8:
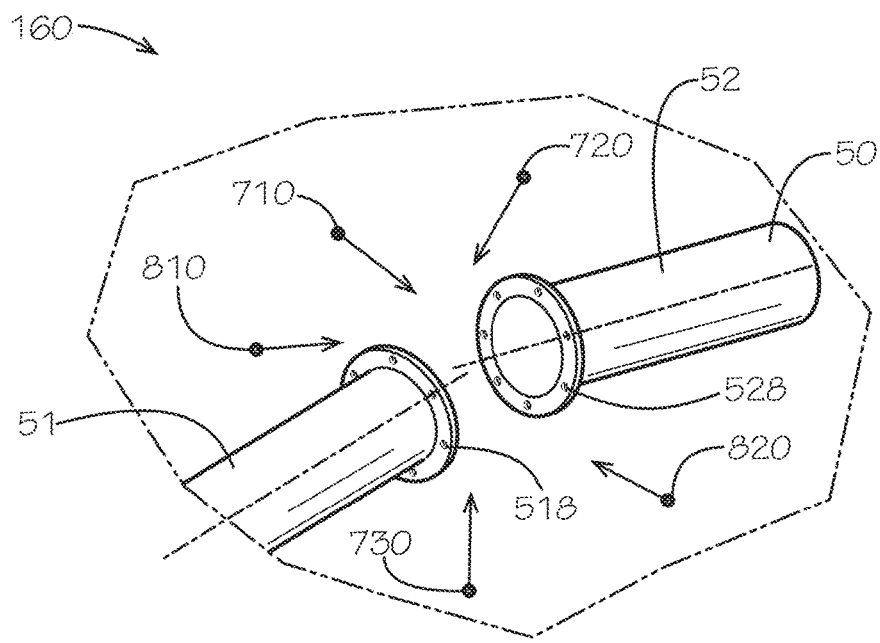
FIG. 8 is a perspective view of the water infrastructure system of FIG. 7.

FIG. 8 is a perspective view of the water infrastructure system of FIG. 7 showing additional scanning positions 810, 820. In some aspects, only a single scanning process is necessary. In other aspects, multiples scanning processes from several scanning positions 710, 720, 730, 810, 820 can be performed. Once the data resulting from the scanning process(es) are "reconstructed," i.e., converted into 3D geometry usable by the manufacturing unit 330, a device such as, for example and without limitation, a 3D printer can directly fabricate the component 62 or can indirectly fabricate the component 62 by, for example and without limitation, a 3D sand printing process described above.

Figure 9:
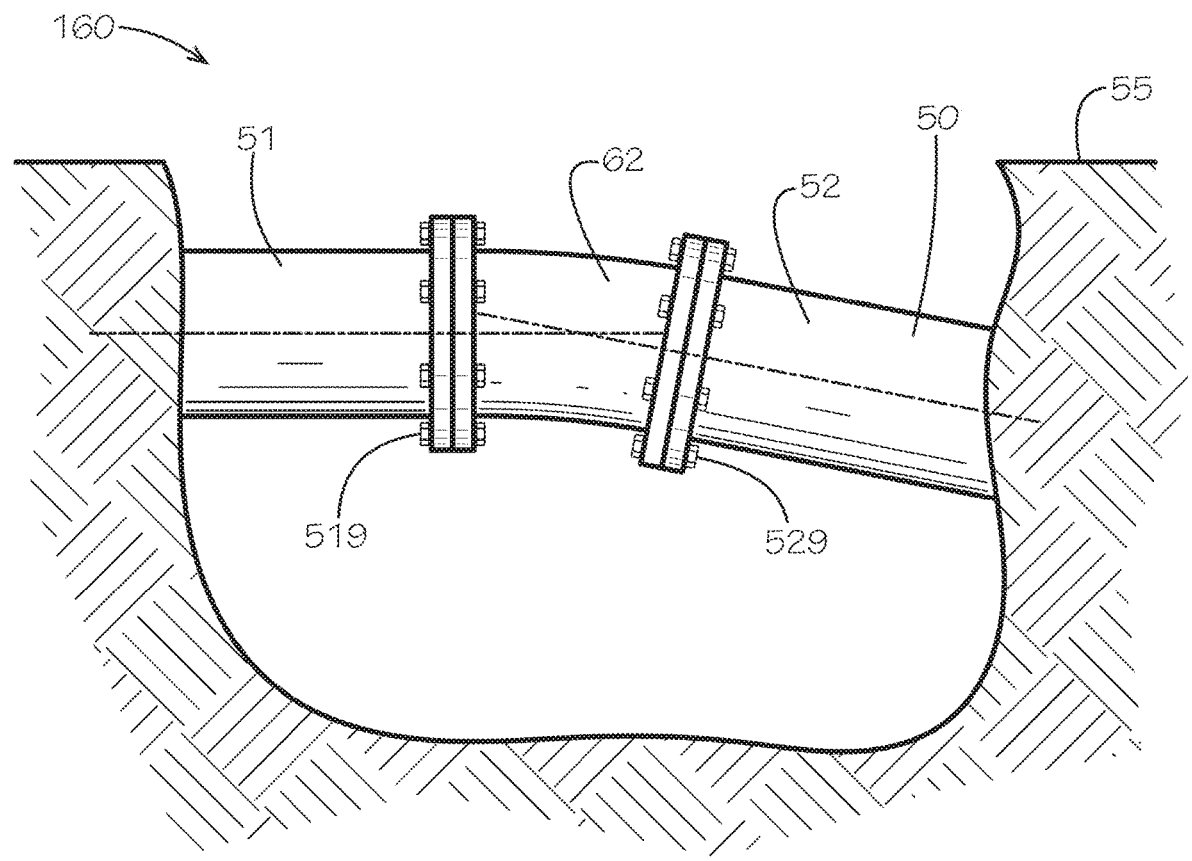
FIG. 9 is a side view of the water infrastructure system of FIG. 7 with a fitting fabricated by the mobile manufacturing platform and installed using the mobile manufacturing system.
Figure 10:
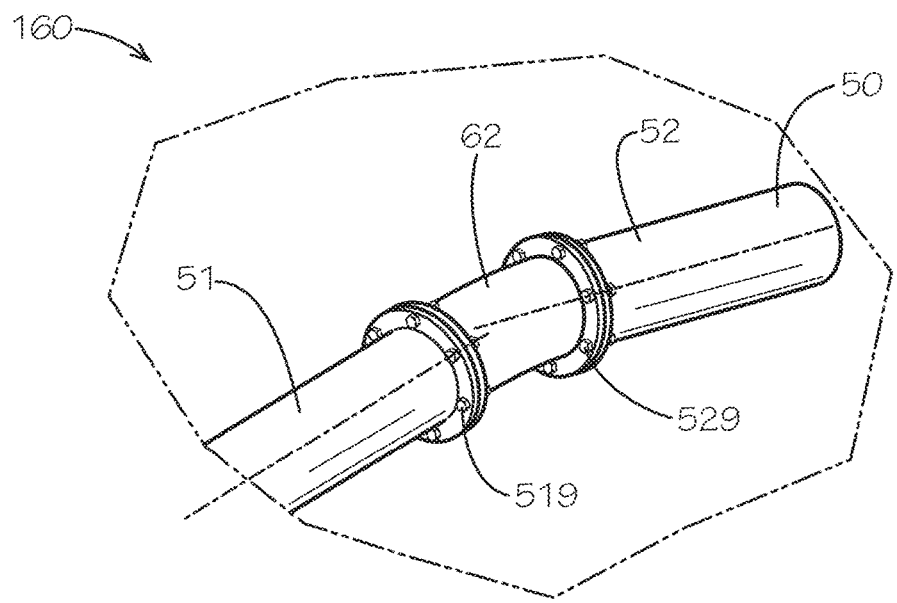
FIG. 10 is a perspective view of the water infrastructure system of FIG. 9.

FIGS. 9 and 10 show the water infrastructure system 50 with the completed component 62 installed therein. A plurality of fasteners 519, 529, which can be stored in the material storage unit 120 (shown in FIG. 1) and delivered to the worksite 160 by the transport device 140 (e.g., a drone or a truck or any other vehicle), can be used to join and secure the component 62 to the respective pipes 51, 52. The water infrastructure system 50 can then be returned to service.

Figure 11:
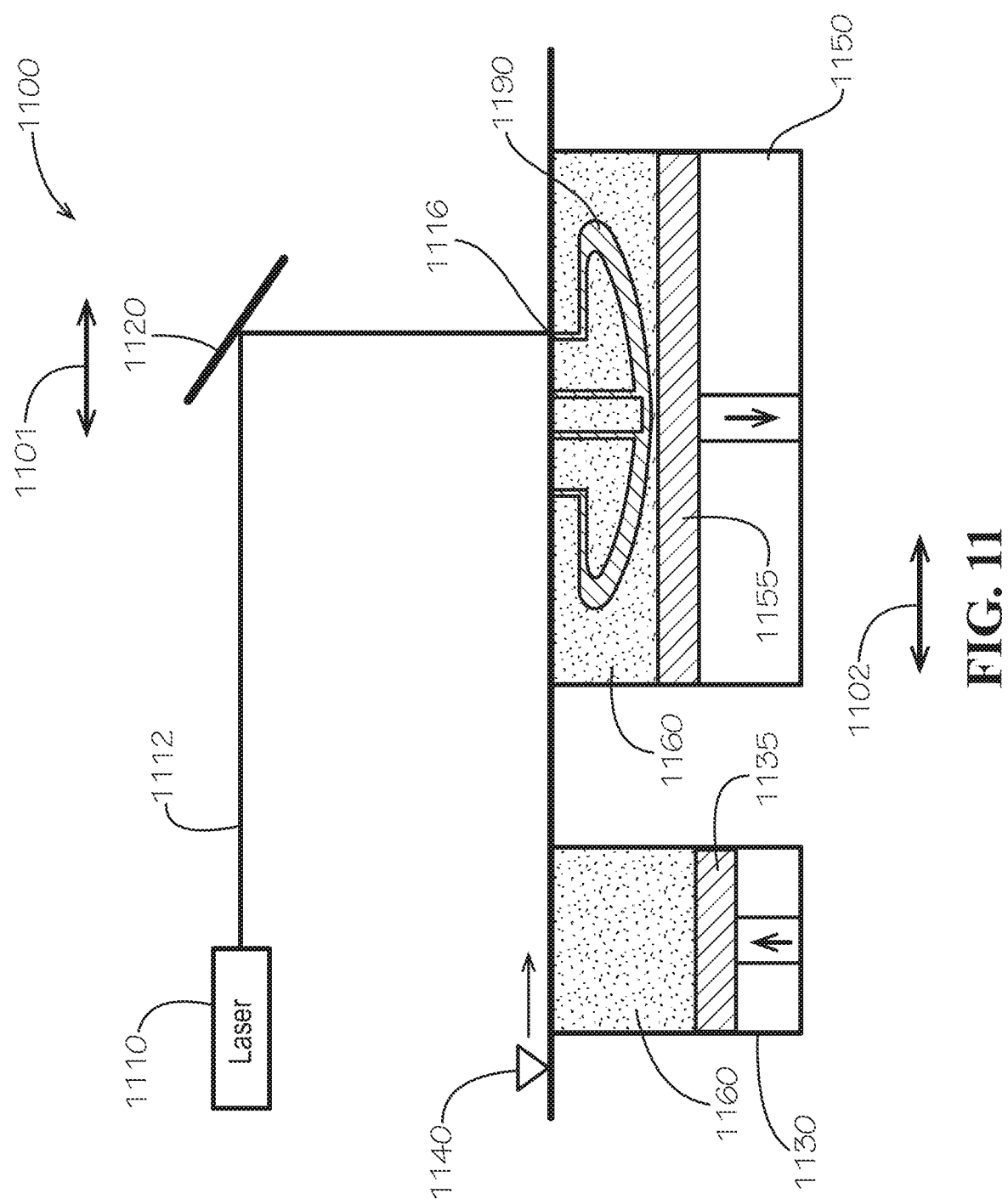
FIG. 11 is a partial sectional side view of an additive manufacturing system using a selective laser melting (SLM) process in accordance with one aspect of the current disclosure.

FIG. 11 shows one example of an additive manufacturing system 1100 configured to perform a selective laser melting (SLM) process to produce an object 1190 (which can be a component 61, 62). As referenced above, the SLM process can be considered a powder bed process of additive manufacturing. The additive manufacturing system 1100 can comprise a laser 1110 that produces a beam 1112, a mirror 1120, a powder delivery system 1130, a roller or blade 1140, and a build space or build system 1150. The beam 1112 can be directed towards a burning point 1116 of a surface of the build system 1150 by tilting and focusing a mirror 1120 as needed. The powder delivery system 1130, configured to deliver powder 1160 to the build system 1150, can comprise a powder delivery piston 1135 that can be raised as shown to maintain the supply of the powder 1160. The build system 1150 can comprise a fabrication piston 1155 that can be lowered in the vertical direction as shown to lower the object 1190 as successive layers are added using the process.

The selective laser melting process starts by slicing the three-dimensional solid model (i.e., the three-dimensional CAD model) into layers, typically from 20 to 100 micrometers thick, creating a two-dimensional (2D) image of each layer using, for example and without limitation, an industry standard format such as the STL file format used in many layer-based 3D printing or stereolithography technologies. The resulting file is then loaded into a file preparation software package that assigns parameters, values and physical supports that allow the file to be interpreted and built by various types of additive manufacturing systems such as the additive manufacturing system 1100 shown.

In the SLM process, thin layers of atomized fine metal powder can be evenly distributed using a coating mechanism onto a substrate plate, often metal, which can be fastened to the fabrication piston 1155. This process can take place inside a chamber containing a tightly controlled atmosphere of inert gas such as, for example and without limitation, argon or nitrogen at oxygen levels below 500 parts per million. Once each layer has been distributed, each 2D slice of the part geometry can be fused by selectively melting the powder. This can accomplished with the beam 1112, which can be produced by a fiber laser with hundreds or even thousands of watts. The beam 1112 can be directed in the X-direction 1101 and Y-direction (not shown) with the mirror 1120. The laser energy can be made intense enough to permit full melting (and thus welding) of the particles to form solid metal. The process can be repeated layer after layer until the object 1190 has been completely formed.

The blade 1140, which can be a roller in other aspects, can be used to transfer powder from the powder delivery system to the build system 1150. In some aspects, the mirror 1120 can be moved in the X-direction 1101 to move the burning point 1116 in the X-direction. In other aspects, the build system 1150 can be moved in the X-direction 1102 to produce the same result. After the build process is complete, the unused powder around the object 1190 can be blown or cleaned away.

Compared to additive manufacturing processes such as the SLM process, traditional manufacturing processes can have a relatively high set-up cost (e.g., for creating a mold). While the object 1190 when made by the SLM process can have a higher piece price because of the time required to build the part (compared to a single shot molding or casting process, for example), it can nonetheless be a useful method, including when only a few parts are to be produced or one part is to be produced.

Other processes, such as the selective laser sintering (SLS) process, can heat the powder up to a specific point where the powder grains can fuse together but without fully melting the powder into a more homogeneous part as in the SLM process.

It is contemplated that the operator of the mobile manufacturing platform 100 or a remote user of the system 90 can modify scanned geometry of the component 61, 62 or geometry for a component 61, 62 downloaded from the server 110 using a 3D computer-aided drafting (CAD) program or other program operating on or in communication with the mobile manufacturing platform 100. The operator or the user can make these modifications onsite at the worksite 160 or remotely by inputting certain variables (e.g., wall thickness), incorporating desired features (e.g., lifting lugs for heavier parts or reinforcement ribs for components 61, 62 that the user or technician knows may be subjected to certain loads) or to otherwise improve, update per recent code, or otherwise modify the base design. In some aspects, such as when no existing part is available (such as shown in FIG. 7), the operator or the user can design such a part "from scratch" or from a generic model such as a parametric model in the aforementioned Pro/Engineer software (also known as PTC/Creo), which can enable the operator or the user to combine the dimensions or data captured at the worksite 160 with the design intent captured already in the generic model by simply adjusting certain dimensions in the model, assembling in virtual space such as using Pro/Engineer to check for fit, and continuing with any one or more of the processes or methods described herein. In other aspects, an AI engine can perform steps that would otherwise be performed by the operator or the user by learning about the system 90, searching for and downloading any data on the required specifications from the server 110, and going through any one or more of the processes or methods described herein.

One should note that conditional language, such as, among others, "can," "could," "might," or "may," unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily comprise logic for deciding, with or without user input or prompting, whether these features, elements and/or steps are included or are to be performed in any particular aspect.

It should be emphasized that the above-described aspects are merely possible examples of implementations, merely set forth for a clear understanding of the principles of the present disclosure. Any process descriptions or blocks in flow diagrams should be understood as representing modules, segments, or portions of code which comprise one or more executable instructions for implementing specific logical functions or steps in the process, and alternate implementations are included in which functions may not be included or executed at all, may be executed out of order from that shown or discussed, including substantially concurrently or in reverse order, depending on the functionality involved, as would be understood by those reasonably skilled in the art of the present disclosure. Many variations and modifications may be made to the above-described aspect(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

That which is claimed is:

1. A mobile manufacturing system comprising:
   a control unit configured for ready portable transport via a vehicle from a storage site to a worksite and then back to the storage site, the worksite located remotely from the storage site;
   a three-dimensional scanner operatively coupled to the control unit and configured for portable transport via the vehicle to the worksite, the scanner configured to convert geometry of a first component of a water infrastructure system into electronic data based on a physical scan of the first component, a one of the scanner and the control unit comprising a converter configured to convert the data into a three-dimensional solid model of the first component;
   a manufacturing unit operatively coupled to the control unit and configured for ready portable transport via the vehicle to the worksite, the manufacturing unit configured to fabricate a second component of the water infrastructure system using an automated manufacturing process based on the solid model of the first component; and
   a quality test unit operatively coupled to the control unit and configured to perform testing on the second component and on dog bone samples of a batch of a material used to fabricate the second component.

2. The system of claim 1, wherein the control unit is configured to operatively couple to a server comprising a computer-readable storage medium, the computer-readable storage medium configured to selectively store data sufficient for defining at least a portion of specifications of the first component, the manufacturing unit further configured to fabricate the second component of the water infrastructure system using the portion of specifications of the first component stored on the computer-readable storage medium of the server.

3. The system of claim 2, wherein the server is further configured to selectively send the data to and receive the data from a certification agency.

4. The system of claim 1, further comprising a material storage unit configured to store at least one of raw materials, partially fabricated parts, and fabricated parts for use by the system.

5. The system of claim 4, further comprising a transport device configured to transport the at least one of the raw materials, the partially fabricated parts, and the fabricated parts from the material storage unit to the worksite.

6. The system of claim 1, further comprising a power unit configured to power at least one of the control unit, the scanner, and the manufacturing unit.

7. A mobile manufacturing system comprising:
   a server comprising a computer-readable storage medium, the computer-readable storage medium configured to selectively store data sufficient for defining at least a portion of specifications of a first component, the server further configured to selectively send the data to and receive the data from a certification agency; and a mobile manufacturing platform configured for transport via a vehicle to a worksite, the platform comprising:
  a control unit operatively coupled to the server;
  a three-dimensional scanner operatively coupled to the control unit, the scanner configured to convert geometry of the first component into electronic data based on a physical scan of the first component; a one of the control unit and the scanner comprising a converter configured to convert the data into a three-dimensional solid model of the first component;
  a manufacturing unit operatively coupled to the control unit, the manufacturing unit configured to fabricate a second component using an automated manufacturing process based on the solid model of the first component stored on the server;
  a quality test unit operatively coupled to the control unit and configured to perform testing on the second component and on dog bone samples of a batch of a material used to fabricate the second component;
  a material recycle unit operatively coupled to the control unit and configured to receive the first component for disposal; and
  a power unit configured to power at least one of the control unit, the scanner, the manufacturing unit, the quality test unit, and the material recycle unit; the power unit comprising a power source comprising at least one of a battery and a generator.

8. The system of claim 7, wherein the manufacturing unit comprises a three-dimensional printer.

9. The system of claim 7, wherein the quality test unit comprises a tensile test unit configured to perform tensile testing on the dog bone samples of the batch of a material used to fabricate the second component.

10. The system of claim 7, further comprising:
  a material storage unit configured to store at least one of raw materials, partially fabricated parts, and fabricated parts for use by the manufacturing unit in fabricating the second component; and
  a transport device configured to transport the at least one of the raw materials, the partially fabricated parts, and the fabricated parts from the material storage unit to the worksite, the transport device being an unmanned aerial vehicle.

11. A method of manufacturing a component of a water infrastructure system, the method comprising:
  carrying a mobile manufacturing platform with a vehicle from a storage site to a worksite located remotely from the storage site, the mobile manufacturing platform comprising:
    a control unit;
    a manufacturing unit operatively coupled to the control unit; and
    a quality test unit comprising a tensile test unit;
  sending a three-dimensional solid model of a first component or an equivalent thereof to the manufacturing unit;
  fabricating a second component using an automated manufacturing process based on the solid model of the first component saved on a computer-readable storage medium operatively coupled to the control unit;
  fabricating a dog bone sample from a batch of a material used to fabricate the second component;
  performing tensile testing on the dog bone sample;
  comparing a tensile strength of the dog bone sample with a reference strength of the material used to fabricate the second component;
  alerting a user of the system as to whether the tensile strength of the dog bone sample is within an acceptable range about the reference strength of the material; and
  returning the system from the worksite to the storage site.

12. The method of claim 11, wherein the platform further comprises a three-dimensional scanner operatively coupled to the control unit, the method further comprising:
  scanning into electronic data with the scanner three-dimensional geometry of the first component, a one of the control unit and the scanner comprising a converter;
  converting the data into the solid model of the first component using the converter;
  sending the data from the control unit to a server comprising the computer-readable storage medium; and
  storing the data on the computer-readable storage medium.

13. The method of claim 11, further comprising sending data on the component to a certification agency.

14. The method of claim 11, further comprising:
  storing at least one of raw materials, partially fabricated parts, and fabricated parts in a material storage unit located separately from the worksite and the vehicle; and
  transporting the at least one of the raw materials, the partially fabricated parts, and the fabricated parts from the material storage unit to the worksite.

15. The method of claim 11, wherein the manufacturing unit further comprises a three-dimensional printer, the method comprising fabricating the second component with the printer.

16. The method of claim 11, wherein the mobile manufacturing platform further comprises a material recycle unit operatively coupled to the control unit, the method further comprising:
  receiving the first component for disposal within the material recycling unit; and
  converting the first component into a recyclable form.

17. The method of claim 11, further comprising tagging the second component with a digital signature that provides information about the second component.

18. The method of claim 11, further comprising scanning the first component with a spectrometer to identify a specification of a material forming the first component.

* * * * *